United States Patent [19]

Manoury et al.

[11] Patent Number: 4,680,296
[45] Date of Patent: Jul. 14, 1987

[54] PIPERIDINE DERIVATIVES AND PHARMACEUTICAL COMPOSITIONS CONTAINING THEM

[75] Inventors: Philippe Manoury, Verrieres le Buisson; Jean Binet, Breuillet; Elisabeth Dewitte, St Gratien, all of France

[73] Assignee: Synthelabo, Paris, France

[21] Appl. No.: 787,971

[22] Filed: Oct. 15, 1985

[30] Foreign Application Priority Data

Oct. 16, 1984 [FR] France ............................ 84 15847
Jul. 10, 1985 [FR] France ............................ 85 10533
Jul. 10, 1985 [FR] France ............................ 85 10534
Jul. 10, 1985 [FR] France ............................ 85 10535

[51] Int. Cl.$^4$ .................. A61K 31/505; C07D 401/04
[52] U.S. Cl. .................................... 514/259; 514/318; 514/322; 544/285; 544/250; 546/192; 546/193; 546/194; 546/199; 546/212; 546/237; 548/305
[58] Field of Search ............... 544/285; 546/199, 194; 514/259, 318, 322

[56] References Cited

U.S. PATENT DOCUMENTS 3,879,393  4/1975  Havera .......................... 546/199
4,016,166  4/1977  Noda et al. ..................... 544/285
4,588,722  5/1986  Janssens et al. ................. 546/199

Primary Examiner—Glennon H. Hollrah
Assistant Examiner—James H. Turnipseed
Attorney, Agent, or Firm—Wegner & Bretschneider

[57] ABSTRACT

Piperidine derivatives which are compounds of formula (I)

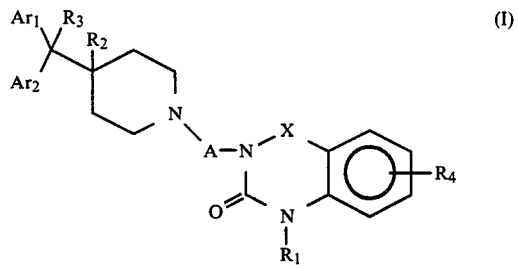

wherein $Ar_1$ and $Ar_2$ independently represent a phenyl group optionally substituted by a halogen atom, a thienyl group or a pyridinyl group, A represents an alkylene group of 2 to 6 carbon atoms, X represents a CO group or a bond, $R_1$ represents a hydrogen atom or an alkyl group of 1 to 4 carbon atoms, either $R_2$ represents a hydrogen atom and $R_3$ represents a hydrogen atom or a hydroxy group, or $R_2$ and $R_3$ together represent a bond, and $R_4$ represents a hydrogen or halogen atom, or pharmaceutically acceptable acid addition salts thereof are useful as antiallergics and antipruritics.

5 Claims, No Drawings

PIPERIDINE DERIVATIVES AND PHARMACEUTICAL COMPOSITIONS CONTAINING THEM

The present invention relates to piperidine derivatives, their preparation and to pharmaceutical compositions containing them.

The invention provides piperidine derivatives which are compounds of formula (I)

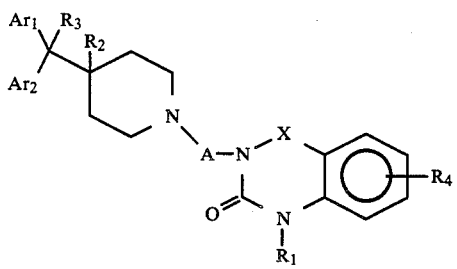

wherein $Ar_1$ and $Ar_2$ independently represent a phenyl group optionally substituted by a halogen atom, a thienyl group or a pyridinyl group, A represents an alkylene group of 2 to 6 carbon atoms, X represents a CO group or a bond, $R_1$ represents a hydrogen atom or an alkyl group of 1 to 4 carbon atoms, either $R_2$ represents a hydrogen atom and $R_3$ represents a hydrogen atom or a hydroxy group, or $R_2$ and $R_3$ together represent a bond, and $R_4$ represents a hydrogen or halogen atom, or pharmaceutically acceptable acid addition salts thereof.

The preferred piperidine derivatives of the invention are those in which $Ar_1$ and $Ar_2$ independently represent a 2-thienyl, 2-pyridinyl, phenyl or 4-fluorophenyl group and $R_4$ represents a hydrogen atom, with the other symbols being as defined above.

Preferably $R_2$ is a hydrogen atom and $R_3$ is a hydroxy group. Also preferred are those derivatives wherein $Ar_1$ denotes a 4-fluorophenyl group and $Ar_2$ denotes a 4-fluorophenyl group or a 2-pyridinyl group.

According to the invention the piperidine derivatives are prepared by reacting a compound of formula (II)

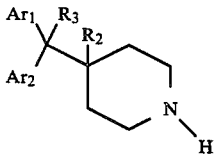

with a compound of formula (III)

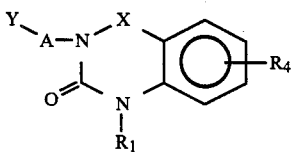

wherein Y is a halogen atom or a labile group and the various other symbols are as defined above, in a protic or aprotic solvent at a temperature of 25° to 120° C., and if desired converting the resulting compound of formula (I) into an acid addition salt in manner known per se.

When Y is a labile group it preferably is tosyl or mesyl. Suitable protic solvents are alcohols and suitable aprotic solvents include methyl isobutyl ketone.

Some of the compounds of formula (II) are described in U.S. Pat. No. 2,804,422 and in the literature by Duncan et al., J. Med. Chem. 13, 1, 1970.

Compounds (II) in which $Ar_1$ or $Ar_2$ represents a pyridinyl or phenyl group may be prepared by reacting a compound of formula (IV)

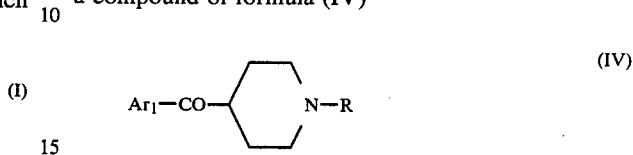

wherein R is a protective group such as acetyl or benzyl, with an organometallic compound of formula (V)

and then hydrolyzing or hydrogenolyzing the resulting compound (VI)

to produce a compound (II).

The compounds (III) are described in the literature, by Vernin et al., J. Het. Chem., 18, 85 (1981).

Compounds of formula (I) in which $R_2 = R_3 = H$ may also be obtained by hydrogenolysis of compounds of formula (I) in which $R_2 = H$ and $R_3 = OH$ or hydrogenation of compounds of formula (I) in which $R_2$ and $R_3$ together represent a bond.

The compounds (I) in which X is CO, $R_1 = H$ and A is $(CH_2)_2$ may be prepared by reacting a compound of formula (VII)

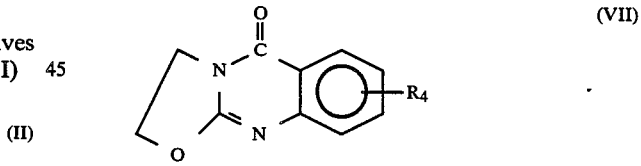

with a compound of formula (II) in a solvent such as toluene or methyl isobutyl ketone.

The compounds of formula (VII) are described in the literature.

The following Examples will serve to illustrate the invention.

The structures of the compounds were confirmed by analyses and IR and NMR spectra.

EXAMPLE 1

1-[2-[4-(Hydroxydiphenylmethyl)-1-piperidinyl]-ethyl]-1,3-dihydro-2(2H)-benzimidazolone A mixture of 2.7 g (0.01 mole) of alpha,alpha-diphenyl-4-piperidinemethanol, 2.4 g (0.01 mole) of 1-(1-bromo-2-ethyl)-2-benzimidazolone, 1.2 g of sodium carbonate ($Na_2CO_3$), and a crystal of sodium iodide in 75 ml of methyl isobutyl ketone is heated at reflux temperature for 18 h.

The mixture is cooled and then evaporated to dryness. The evaporation residue is taken up with a mixture of water and chloroform and the organic phase is dried, filtered and evaporated. Compound (I) is obtained, which is recrystallized from an ethyl acetate/isopropyl ether (85/15) mixture. M.p.=193°–196° C.

EXAMPLE 2

1-[2-[4-(Diphenylmethylene)-1-piperidinyl]-ethyl]-1,3-dihydro-2(2H)-benzimidazolone Methyl isobutyl ketone, 1.0 g (0.004 mole) of 4-(diphenylmethylene)piperidine, 0.96 g (0.004 mole) of 1-(1-bromo-2-ethyl)-2-benzimidazolone, 0.53 g (0.008 mole) of Na$_2$CO$_3$ and a few crystals of NaI are heated for 9 h at the reflux temperature.

The solvent is evaporated off, the residue is taken up with water and methylene chloride, the reaction mixture is separated by gravity, and the organic phase is dried and evaporated. A yellow solid is obtained which is passed through a column of silica (eluant 97 CH$_2$Cl$_2$/3 MeOH). On evaporation a solid is collected which is recrystallized from ethyl acetate. M.p.=202°–203° C.

EXAMPLE 3

1-[2-[4-Diphenylmethyl-1-piperidinyl]ethyl]-1,3-dihydro-2(2H)-benzimidazolone

A solution of 4 g of 1-[2-[4-diphenylmethylene-1-piperidinyl]ethyl]-1,3-dihydro-2(2H)-benzimidazolone in 150 cm$^3$ of methanol is hydrogenated with the aid of a Parr apparatus, at ambient temperature, at a hydrogen pressure of 50 psi, in the presence of 5% palladium on charcoal. When the absorption of hydrogen has ended, the catalyst is filtered off and the filtrate is evaporated down. The product obtained is recrystallized from ethyl acetate. M.p.=195°–196° C.

EXAMPLE 4

1-[2-[4-[Bis(4-fluorophenyl)methyl]-1-piperidinyl]ethyl]-1,3-dihydro-2(2H)-benzimidazolone.

Methyl isobutyl ketone, 1.6 g (0.006 mole) of 1-(1-bromo-2-ethyl)-1,3-dihydro-2(2H)-benzimidazolone, 1.9 g (0.0066 mole) of bis(4-fluorophenyl)-4-methylpiperidine, 0.8 g (0.0075 mole) of Na$_2$CO$_3$ and a few crystals of NaI are heated at reflux temperature for approximately 6 h. The solvent is evaporated off, the residue is taken up with a mixture of ether and water, the reaction mixture is allowed to undergo phase separation, and the ether phase is filtered and evaporated down. An oil is obtained which is crystallized from isopropyl ether. A pure white product is filtered off and dried. M.p.=104°–106° C.

EXAMPLE 5

1-[3-[4-[Bis-(4-fluorophenyl)hydroxymethyl]-piperidinyl]propyl]-1,3-dihydro-2(2H)-benzimidazolone 2.1 g (0.007 mole) of 4-[bis(4-fluorophenyl)hydroxymethyl]piperidine, 1.8 g (0.007 mole) of 1-(1-bromo-3-propyl)-1,3-dihydro-2(2H)-benzimidazolone, 0.85 g (0.008 mole) of Na$_2$CO$_3$ and a few crystals of NaI are heated for 5 h at reflux temperature in 60 ml of methyl isobutyl ketone. The solvent is evaporated off, the residue is taken up with a mixture of water and CH$_2$Cl$_2$, and the organic phase is dried and evaporated down. A solid residue is obtained which is chromatographed on a column of silica (eluent: CH2Cl2/MeOH 97/3, 96/4 and then 94/6). The pure fractions are evaporated down, the evaporation residue is taken up with ether and a white product is filtered off and crystallized from 90 ml of ethyl acetate. M.p.=141°–143° C.

EXAMPLE 6

1-[2-[4-[(2-Pyridinyl)(phenyl)hydroxymethyl]-piperidinyl]ethyl]-1,3-dihydro-2(2H)-benzimidazolone 1.1. 4-[(2-Pyridinyl)(phenyl)hydroxymethyl]piperidine 1.1.1.
4-[(2-Pyridinyl)(phenyl)hydroxymethyl]-1-benzylpiperidine 2.1 ml (2.2 10$^{-2}$ mole) of 2-bromopyridine in solution in 10 ml of tetrahydrofuran (THF) are added dropwise to a solution, cooled to −65° C., of 15.6 ml (2.5 10$^{-2}$ mole) of n-BuLi and of 20 ml of THF. The mixture is stirred for ¼ h at −65° C. and then 5.6 g (2 10$^{-2}$ mole) of 1-benzyl-4-benzoylpiperidine in 20 ml of THF are added dropwise while the temperature is maintained at −65° C. The mixture is allowed to warm up very slowly and is then left overnight. It is heated to the reflux temperature for 2 h and then evaporated to dryness, and the residue is taken up with a mixture of water and ether. The ether phase is washed with water, dried, filtered and evaporated down. Chromatography on silica is carried out (eluent 95/5 CH$_2$Cl$_2$/MeOH). A product which crystallizes from petroleum ether is collected. M.p.=142°–143° C.

1.1.2.
4-[(2-Pyridinyl)(phenyl)hydroxymethyl]piperidine 5.4 g (1.5 10$^{-2}$ mole) of the derivative obtained previously, in solution in 50 ml of methanol containing 1 ml of acetic acid, are hydrogenated, in a Parr apparatus, at 40° C., in the presence of palladium on charcoal, at a pressure of 0.35 Mpa. When the absorption is finished, the catalyst is filtered off and the mixture is then evaporated to dryness.

The residue is taken up with a little water, made alkaline with sodium hydroxide and extracted with ether. It is dried, filtered and evaporated down.

The product, which crystallizes in isopropyl ether, is triturated. M.p.=125°–128° C.

1.2.
1-[2-[4-[(2-Pyridinyl)(phenyl)hydroxymethyl]-1-piperidinyl]ethyl]-1,3-dihydro-2(2H)-benzimidazolone 2.5 g (10$^{-2}$ mole) of 4-[(2-pyridinyl)(phenyl)hydroxymethyl]piperidine, 2.5 g (10$^{-2}$ mole) of 1-(1-bromo-2-ethyl)-1,3-dihydro-2(2H)-benzimidazolone, 1.2 g of Na$_2$CO$_3$, one crystal of NaI and 75 ml of methyl isobutyl ketone are introduced into a round flask.

The mixture is maintained at reflux temperature for 4 h and is evaporated to dryness; the residue is taken up with a mixture of water and methylene chloride; the organic phase is dried, filtered and evaporated down. After trituration in ether, a product is obtained which is recrystallized from methyl ethyl ketone. M.p.=206°–207° C.

EXAMPLE 7

3-[2-[4-[Diphenylhydroxymethyl]-1-piperidinyl]ethyl]-2,4(1H,3H)-quinazolinedione 2 g (0.00748 mole) of 4-(diphenylhydroxymethyl)-piperidine and 1.4 g (0.00748 mole) of 2,3-dihydro(2,5- b)(5H)oxazolo-5-quinolinone in 50 ml of toluene containing one drop of 7.5 N hydrochloric acid are introduced into a 100 ml three-necked round flask. The mixture is heated at 100°–120° C. for 28 h.

The precipitate formed is filtered off, washed with a little toluene and dried. The compound is recrystallized from methanol. M.p.=206°–208° C.

EXAMPLE 8

1-[3-[4-(Diphenylhydroxymethyl)-1-piperidinyl]-propyl]-2,4-(1H,3H)-quinazolinedione 2.7 g (0.01 mole) of 4-(diphenylhydroxymethyl) piperidine, 1.2 g (0.005 mole) of 1-(3-chloropropyl)-2,4(1H,3H)-quinazolinedione in 75 ml of ethanol are heated at reflux temperature for 7 h.

The precipitate is filtered off, taken up with a mixture of water and $CHCl_3$, made alkaline with sodium hydroxide, stirred for half an hour and filtered off. The compound is recrystallized from pyridine. M.p.=248°–250° C.

The compounds prepared by way of examples are shown in the following table.

On three-coloured male guinea-pigs weighing approximately 300 g, after 18 hours-fasting.

A fragment of ileum is removed, placed at 39° C. in a tyrode bath at 39° C. through which a stream of carbonating gas (95% $O_2$, 5% $CO_2$) is passing and connected to an isotonic sensor with a maximum tension of 2.5 g. The contractions are recorded by means of an Ugo Basile microdynamometer.

The contractions are induced by various spasmogenic agents for which the concentration causing a submaximal response is determined (histamine: 1 to 8 $10^{-8}$ g/ml). The piperidine derivatives of the invention, dissolved in distilled water or a 0.1 N solution of methanesulfonic acid, are placed in contact with the ileum for 1 min before the introduction of the spasmogenic substance. The $AC_{50}$ (concentration reducing by 50% the contractions induced by histamine) of certain piperidine derivatives of the invention range from $10^{-7}$ to $10^{-8}$ molar.

2. Activity in vivo: Inflammation induced by histamine or serotonin.

Intraplanar injection of histamine(200 μg)or of serotonin (1 μg) into one of the hind paws of the rat causes an oedema measured, 1 h after injection, with the aid of a mercury Ugo Basile plethysmometer.

The piperidine derivatives of the invention, suspended in a 1% solution of Tween in distilled water are

TABLE

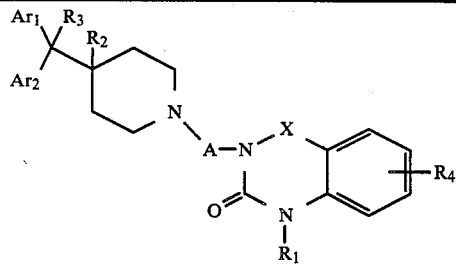

| Compound | X | A | Ar$_1$ | Ar$_2$ | R$_1$ | R$_2$ | R$_3$ | R$_4$ | M.p (°C.) |
|---|---|---|---|---|---|---|---|---|---|
| 1 | bond | (CH$_2$)$_2$ | C$_6$H$_5$ | C$_6$H$_5$ | H | H | H | H | 195–196 |
| 2 | bond | (CH$_2$)$_2$ | C$_6$H$_5$ | C$_6$H$_5$ | H | | bond | H | 202–203 |
| 3 | bond | (CH$_2$)$_2$ | C$_6$H$_5$ | C$_6$H$_5$ | H | H | OH | H | 193–196 |
| 4 | bond | (CH$_2$)$_2$ | C$_6$H$_5$ | C$_6$H$_5$ | CH$_3$ | H | OH | H | 166–170 |
| 5 | bond | (CH$_2$)$_2$ | C$_6$H$_5$ | C$_6$H$_5$ | iPr | H | OH | H | 140–142 |
| 6 | bond | (CH$_2$)$_3$ | C$_6$H$_5$ | C$_6$H$_5$ | H | H | OH | H | 180–182 |
| 7 | bond | (CH$_2$)$_4$ | C$_6$H$_5$ | C$_6$H$_5$ | H | H | OH | H | 95 |
| 8 | bond | (CH$_2$)$_5$ | C$_6$H$_5$ | C$_6$H$_5$ | H | H | OH | H | 114–117 |
| 9 | bond | (CH$_2$)$_2$ | 4-F—C$_6$H$_4$ | 4-F—C$_6$H$_4$ | H | H | H | H | 104–106 |
| 10 | bond | (CH$_2$)$_2$ | 4-F—C$_6$H$_4$ | 4-F—C$_6$H$_4$ | H | H | OH | H | 149–151 |
| 11 | bond | (CH$_2$)$_3$ | 4-F—C$_6$H$_4$ | 4-F—C$_6$H$_4$ | H | H | OH | H | 141–143 |
| 12 | bond | (CH$_2$)$_4$ | 4-F—C$_6$H$_4$ | 4-F—C$_6$H$_4$ | H | H | OH | H | 110 |
| 13 | bond | (CH$_2$)$_3$ | 4-F—C$_6$H$_4$ | C$_6$H$_5$ | H | H | OH | H | 138–140 |
| 14 | bond | (CH$_2$)$_3$ | 4-F—C$_6$H$_4$ | 4-F—C$_6$H$_4$ | H | H | H | H | 165–167 |
| 15 | bond | (CH$_2$)$_3$ | 4-F—C$_6$H$_4$ | 4-F—C$_6$H$_4$ | H | | bond | H | 171–172 |
| 16** | bond | (CH$_2$)$_4$ | 4-F—C$_6$H$_4$ | 4-F—C$_6$H$_4$ | H | H | H | H | 210–212** |
| 17 | bond | (CH$_2$)$_2$ | C$_6$H$_5$ | Pyrid-2 | H | H | OH | H | 206–207 |
| 18 | bond | (CH$_2$)$_3$ | C$_6$H$_5$ | Pyrid-2* | H | H | OH | H | 201–203 |
| 19 | bond | (CH$_2$)$_3$ | 4-F—C$_6$H$_4$ | Pyrid-2 | H | H | OH | H | 192–195 |
| 20 | bond | (CH$_2$)$_2$ | Thienyl-2 | Thienyl-2 | H | H | OH | H | 209–211 |
| 21 | bond | (CH$_2$)$_3$ | Thienyl-2 | Thienyl-2 | H | H | OH | H | 224–226 |
| 22 | bond | (CH$_2$)$_3$ | 4-F—C$_6$H$_4$ | Pyrid-2 | H | H | OH | H | 192–195 |
| 23 | bond | (CH$_2$)$_4$ | 4-F—C$_6$H$_4$ | Pyrid-2 | H | H | OH | H | 69 |
| 24 | CO | (CH$_2$)$_2$ | C$_6$H$_5$ | C$_6$H$_5$ | H | H | OH | H | 206–208 |
| 25 | CO | (CH$_2$)$_3$ | C$_6$H$_5$ | C$_6$H$_5$ | H | H | OH | H | 221–223 |
| 26 | CO | (CH$_2$)$_4$ | C$_6$H$_5$ | C$_6$H$_5$ | H | H | OH | H | 207–208 |
| 27 | CO | (CH$_2$)$_2$ | 4-F—C$_6$H$_4$ | 4-F—C$_6$H$_4$ | H | H | OH | H | 213–214 |
| 28 | CO | (CH$_2$)$_3$ | 4-F—C$_6$H$_4$ | 4-F—C$_6$H$_4$ | H | H | OH | H | 209–212 |
| 29 | bond | (CH$_2$)$_2$ | C$_6$H$_5$ | C$_6$H$_5$ | CH$_3$ | H | OH | Cl | 122–125 |

*Pyrid = Pyridinyl
**melting point of the oxalate

The piperidine derivatives of the invention were subjected to various pharmacological tests to demonstrate their antagonist activity for histamine and for serotonin.

1. Activity in vitro: Isolated guinea-pig ileum

The test was carried out according to the Magnus method modified by Savini (Arch. Int. Pharmacodyn., 113, 157), administered p.o. (0.5 ml/100 g) 1 h before the injection of the inflammatory agent.

The $AD_{40}$ (dose which reduces the volume of the oedema by 40%) are measured.

The piperidine derivatives of the invention have an $AD_{40}$ ranging from 1 to 5 mg/kg when the inflammatory agent is histamine.

Some piperidine derivatives of the invention are active at an $AD_{40}$ dose ranging from 0.2 to 1 mg/kg when the inflammatory agent is serotonin.

The piperidine derivatives of the invention may therefore be employed as antiallergics and antipruritics for the treatment of respiratory allergies, such as rhinitis and hay fever, skin allergies such as dermatitis and urticaria, eye allergies, Quincke's disease and various allergic manifestations.

The piperidine derivatives of the invention which are more specifically active as serotonin antagonists may be employed for combating some undesirable effects of this mediator in the peripheral system or in the central system. They are intended, in particular, for the treatment of migraine.

The invention consequently comprises all pharmaceutical compositions containing, as active ingredient, at least one piperidine derivative of the invention in association with a pharmaceutically acceptable excipient.

The administration routes may be oral or parenteral.

The daily dosage may range from 5 to 200 mg.

We claim:

1. Piperidine derivatives which are compounds of formula (I)

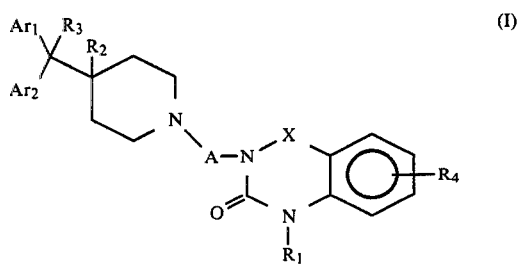

wherein $Ar_1$ and $Ar_2$ independently represent a phenyl group optionally substituted by a halogen atom, a thienyl group or a pyridinyl group, A represents an alkylene group of 2 to 6 carbon atoms, X represents a CO group or a bond, $R_1$ represents a hydrogen atom or an alkyl group of 1 to 4 carbon atoms, either $R_2$ represents a hydrogen atom and $R_3$ represents a hydrogen atom or a hydroxy group, or $R_2$ and $R_3$ together represent a bond, and $R_4$ represents a hydrogen or halogen atom, or pharmaceutically acceptable acid addition salts thereof.

2. Derivatives according to claim 1, wherein $Ar_1$ and $Ar_2$ independently represent a 2-thienyl, 2-pyridinyl, phenyl or 4-fluorophenyl group, and $R_4$ represents a hydrogen atom.

3. Derivatives according to claim 2 wherein $R_2$ is a hydrogen atom and $R_3$ is a hydroxy group.

4. Derivatives according to claim 3 wherein $Ar_1$ denotes a 4-fluorophenyl group and $Ar_2$ denotes a 4-fluorophenyl group or a 2-pyridinyl group.

5. A pharmaceutical composition which contains, as active ingredient, an effective amount of a piperidine derivative as claimed in claim 1 in association with a pharmaceutically acceptable excipient.

* * * * *